United States Patent [19]

Allred, III et al.

[11] Patent Number: 4,836,189

[45] Date of Patent: Jun. 6, 1989

[54] VIDEO HYSTEROSCOPE

[75] Inventors: Jimmie B. Allred, III; Richard A. Kokosa, both of Skaneateles; Allan I. Krauter, Syracuse; Richard W. Newman, Auburn, all of N.Y.

[73] Assignee: Welch Allyn, Inc., Skaneateles Falls, N.Y.

[21] Appl. No.: 244,827

[22] Filed: Jul. 27, 1988

[51] Int. Cl.[4] .......... A61B 1/06

[52] U.S. Cl. .......... 128/6

[58] Field of Search .......... 128/3, 4, 5, 6, 7

[56] References Cited

U.S. PATENT DOCUMENTS

| | | | |
|---|---|---|---|
| Re. 31,289 | 6/1983 | Moore et al. | 128/6 |
| Re. 31,290 | 6/1983 | Moore et al. | 128/6 |
| 3,835,842 | 9/1974 | Iglesias | 128/7 |
| 4,491,865 | 1/1985 | Danna et al. | 128/4 X |
| 4,676,229 | 6/1987 | Krasnicki et al. | 128/4 |
| 4,700,693 | 10/1987 | Lia et al. | 128/4 |
| 4,714,075 | 12/1987 | Krauter et al. | 128/4 |
| 4,754,328 | 6/1988 | Barath et al. | 128/6 X |

*Primary Examiner*—William H. Grieb

[57] ABSTRACT

A video hysteroscope has an elongated flexible insertion tube containing a video imager head at its distal end, with a channel for a surgical laser fiber and a saline channel which emits a continuous stream of saline solution distally from the head. The articulation section is kept as short as possible, and is limited to a maximum deflection of about 30 degrees to match the geometry of the uterus.

14 Claims, 1 Drawing Sheet

VIDEO HYSTEROSCOPE

BACKGROUND OF THE INVENTION

This invention relates to surgical devices, and more particularly to hysteroscopes for the observation and treatment of tissue abnormalities in the uterus of a female patient. The invention is also directed to endoscopic medical instruments in which a video camera is carried at the distal end of a flexible insertion tube.

Present day hysteroscopic techniques involve the use of a rather complex optical system which is inserted vaginally through the cervix, as are surgical instruments. With present day hysteroscopy, in order to observe through the optical system, the surgeon has to keep his or her face close to the affected area of the patient. Also, because of the rigid nature of the hysteroscope, it is possible to work most effectively only in the main body of the uterus, and it is difficult to operate in the horns of the uterus.

An endoscope, and in particular, a gastroscope, is generally characterized as an elongated flexible tube with a viewing head on its distal or forward end, and a control housing at the proximal end for controlling or steering the distal end. In a gastroscope, a bendable steering or articulation section is provided at the distal end adjacent the viewing head. This section extends proximally for a considerable distance to accommodate large bending angles. One or two pairs of control cables extend through the bendable steering section and the remainder of the flexible tube and connect with steering controls in the control section. One or both pairs of these cables are displaced in order to bend the bendable steering section, and thus change the angular orientation of the viewing head. A gastroscope, or any other type of endoscope, is typically inserted into a body cavity of a patient in order to visually investigate the tissues within the cavity. Because the esophagus, stomach, and upper intestinal track are narrow, tortuous passageways, and because of the need for retrospective viewing, the steering section of a gastroscope generally must articulate over an arc of at least 180 degrees. Also, in a gastroscope the insertion tube tends to have a rather stiff proximal section and a softer or more flexible distal section. A limited amount of water and air are channeled through the gastroscope and are directed across the viewing window of the video imager in the viewing head. Such gastroscopes are designed to emit only short bursts of liquid transversely across the glass window of the imager for cleaning of said window.

It would be desirable to employ an endoscope generally of the form of a gastroscope to perform as a hysteroscope for uterine surgery. It would be even more desirable for an endoscope to be insertable up into either of the two horns of the uterus. This would permit a surgeon to observe tissue abnormalities and to treat the same, e.g., with a therapeutic laser. Such a hysteroscopic endoscope should have flexibility which is mild enough to follow the curves of the uterus without damaging the uterine lining, yet stiff enough to permit insertion and accurate manipulation. Such a video endoscope would require a rather short working length, as compared with standard gastroscopes. Ideally, such an endoscopic instrument would employ the video camera in connection with a video monitor to permit a surgeon to work at a position where his or her face is remote from the affected area of the patient. The articulation section should also be as short as possible so that the video imager and laser fiber can be aimed and positioned accurately, even in low clearance areas within the uterine horns.

Unfortunately, no existing endoscopic instrument is suitable for performing such surgery within the uterus, nor has anyone previously adapted a flexible endoscope for this purpose.

OBJECTS AND SUMMARY OF THE INVENTION

It is an object of this invention to provide a flexible video hysteroscope which avoids the drawbacks of the prior art.

It is another object of this invention to provide a medical instrument which permits hysteroscopic microsurgery within portions of the uterus where, with current techniques, such microsurgery cannot now readily be performed.

It is yet another object of this invention to provide a hysteroscope which can be employed with a minimum of discomfort to the patient and a maximum of convenience to the surgeon.

In accordance with an aspect of this invention, a flexible video hysteroscope is provided for observation and treatment of tissue abnormalities in the uterus of a female patient. The hysteroscope has an insertion tube which includes a flexible elongated tubular member having a flexible outer sheath and a viewing head disposed at the distal end of the tubular member. A control assembly is situated at the proximal end. An imager in the viewing head provides a signal representing an image as viewed from the head. A biopsy channel extends within the tubular member to its distal end and through the head, and an elongated flexible laser fiber cable can be inserted to pass up to and out from the head. The laser fiber cable and the biopsy channel define a substantially annular fluid drainage channel that extends from the head to the proximal end of the tubular member. A saline injection channel extends within the flexible tubular member to its distal end and out through the head. This injection channel includes a fitting on the control assembly to receive a continuous flow of aqueous saline solution and also has an outlet port in the head which directs the flow of solution distaly outward from it, rather than across the viewing window of the imager. An articulation section joins the head to the flexible tubular member and permits controlled bending of the head with respect to the flexible tubular member. Here, the bending is limited to a maximum angular deflection of about thirty degrees which corresponds to the angle at which the horns of the uterus attach to the body thereof. Uterine abnormalities are treated by inserting the flexible video hysteroscope vaginally through the cervix of the uterus. Saline solution is supplied through the saline injection channel so that there is a continuous flow of the aqueous saline solution at a maximum rate of about 100 cc per minute distally outward from the head. The effect of this is to inflate the uterus with the clear saline solution, and also to wash away any tissue debris. The head of the flexible hysteroscope is steered by selectively bending the articulation section until a tissue abnormality appears at a predetermined position in the viewing field of the imager. Then, the laser fiber tip is placed in contact with the abnormality and a pulse of laser light is transmitted through the laser fiber to irradiate the abnormality and destroy or cauterize it. The saline solution and any debris carried in it will drain from the uterus through the annular fluid drainage channel defined between the laser fiber cable and the biopsy channel. The flexible tubular member has a uniform predetermined soft flexibility, which, in a preferred embodiment, is substantially 0.2 pounds per inch for a 4 inch cantilevered length.

The above and many other objects, features and advantages of this invention will be more fully understood from the ensuing description of a preferred embodiment, when considered in connection with the accompanying drawing.

DETAILED DESCRIPTION OF A PREFERRED EMBODIMENT

Figure 1:
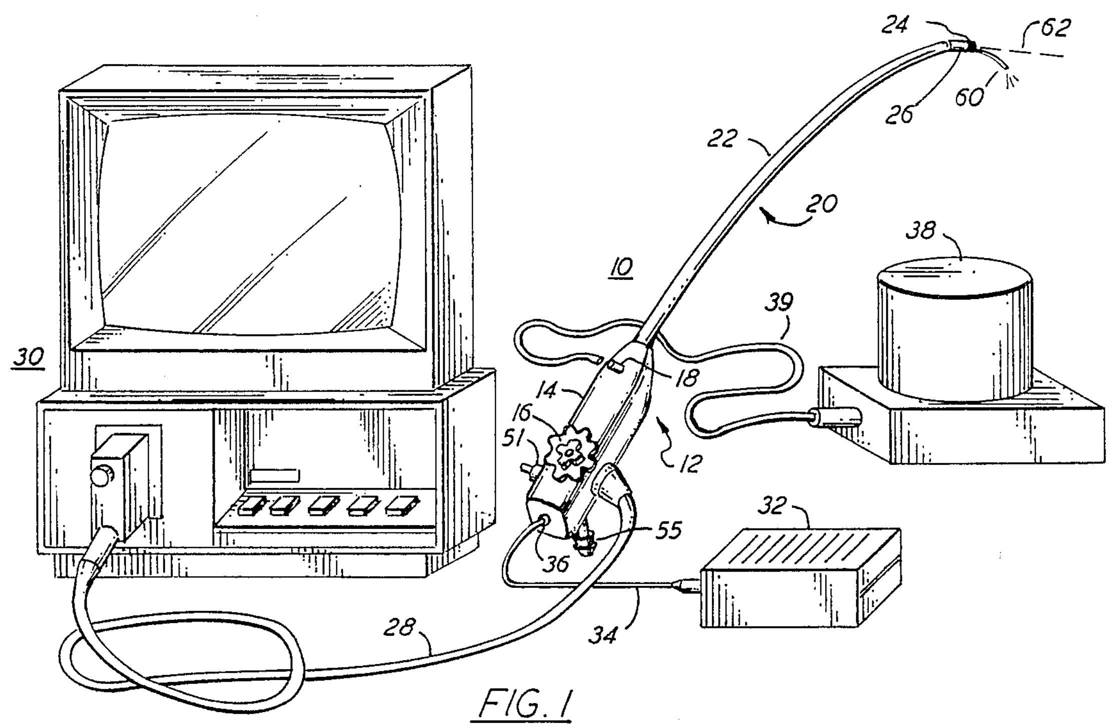
FIG. 1 is a perspective view of video hysteroscope apparatus embodying the principles of this invention.

With reference to the drawing, and initially to FIG. 1, video hysteroscopic apparatus 10 can include a video hysteroscope 12 formed of a control section 14 which has a set of steering control knobs 16 and a saline solution connection 18, and an elongated flexible insertion tube 20 which extends distally from the control section 14. The insertion tube 20 has an elongated flexible tube portion 22, characterized by a flexible sheath, with a viewing head 24 disposed at its distal tip. A steering or articulation section 26 joins the flexible tube portion 22 to the viewing head 24. In order to keep the steering as precise as possible, and to ensure that the bending takes place as close to the distal tip as possible, this steering section 26 is foreshortened relative to the corresponding section of a gastroscopic instrument, and the maximum deflection angle is limited to about thirty degrees.

An umbilical 28 connects the control section 14 to a video processor and monitor 30. A medical therapeutic laser 32 is coupled to an optical fiber cable 34 which is inserted into an opening 36 in the proximal end of the control section 14. A source of saline solution 38 provides an aqueous saline solution under pressure through tubing 39. The latter connects to the connector 18, which is favorably configured as a Luer lock.

The principles of operation of a color video endoscope, including the video processor and monitor 30, are described in reissue Pat. Nos. Re. 31,289 and Re. 31,290. Bendable steering sections are discussed in U.S. Pat. No. 4,700,693.

Figure 2:
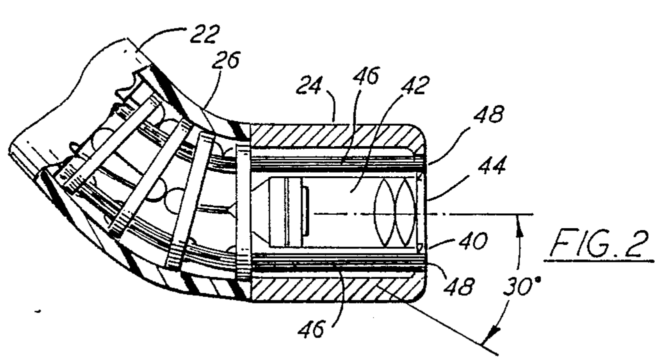
FIG. 2 is a plan view of the head and articulation section of the apparatus, taken along line 2—2 of FIG. 4.
Figure 3:
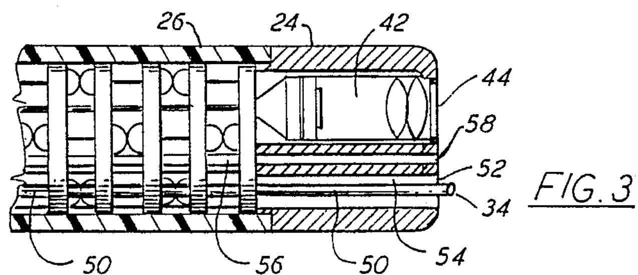
FIG. 3 is a sectional elevation taken along lines 3—3 of FIG. 4.
Figure 4:
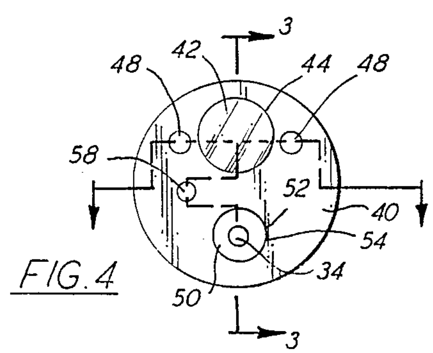
FIG. 4 is a front elevation of the head of the hysteroscopic apparatus of FIG. 1.

As shown in greater detail in FIGS. 2, 3, and 4, the viewing head 24 has a front or distal face 40 behind which is disposed a video imager 42 with an incorporated lens system. Imagers of this type are described, for example, in U.S. Pat. No. 4,491,865. A window 44 for the imager is situated in the face 40 near the top thereof. An optical fiber bundle 46 carries illumination for the imager 42 from a light source in the video processor and monitor 30, and is bifurcated to terminate at a pair of windows 48 which flank the imager window 44.

A biopsy channel 50 extends distally from the opening 36 through the insertion tube 20 to an opening or port 52 beneath the window 44 on the front face 40 of the head 24. The biopsy channel 50 is preferably about three millimeters in diameter, and 15 can be of the type as described in U.S. Pat. No. 4,714,075. The optical fiber cable 34 extends through the channel 50 and up to and through the port 52. The optical fiber cable 34 is of a lesser outer diameter, leaving a substantially annular channel 54 for return fluids to flow out from the uterus to a suction port 55 at the proximal end of the control section 14. This suction port 55 is selectively connected to the channel 50 by means of a suction valve 51 located on the control section 14. The valve 51 is used periodically by the physician when removal of said fluids is desired.

A high pressure saline conduit or channel 56 extends from the connector 18 on the control section 14 distally through the flexible tube portion 22 to a port or jet 58 in the front face 40 of the viewing head 24. As shown in FIG. 4, in the normal, inuse orientation of the hysteroscope 12, the port 58 is below and to one side of the video imager 42 and window 44, and above the position of the biopsy channel port 52. The port 58 provides a continuous arcing jet 60 (FIG. 1) of saline solution at a maximum rate of about 100 cc per minute, with a pressure drop of less than about 155 mm Hg across the length of the channel 56. This pressure represents approximately the maximum pressure available from a stand above the patient being examined or treated. The channel 56 should have a sufficient diameter over its length so that the above flow is maintained. In one embodiment the channel 56 has an inside diameter of substantially 0.050 inches.

The optical fiber laser cable 34 directs a laser beam 62 from the opening 52 in the viewing head front face 40 so that the beam 62 is parallel to and below the axis of the imager 42. In another embodiment of the head 24, means are provided to bend the laser fiber away from the axis of the head. Such bending would increase the ability of a contact laser fiber tip to contact difficult-to-reach regions of the uterus.

The flexible tube portion 22 and viewing head 24 are no more than about 10 mm in diameter, the insertion tube 20 having a working length of about 25 cm. The length of the entire hysteroscope from the head 24 to the opening 36 at the proximal end of the control section 14 is about 55 cm.

The flexible tube portion 22 has a uniform flexibility over its entire length from the control section 14 to the steering section 26. This is measured in terms of the amount of force needed to deflect a four inch cantilevered tube section transversely a distance of one inch. In the preferred embodiment, the flexible tube portion 22 has a stiffness of about 0.2 pounds per inch for a four inch cantilevered length. However, the stiffness can be within a range of 0.05 to 1.0 pounds per inch.

Figure 5:
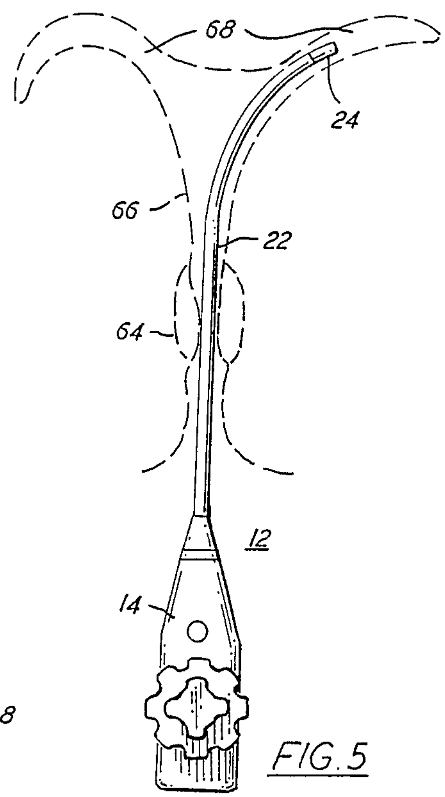
FIG. 5 is a partial perspective view for explaining the use of the hysteroscope of this invention in uterine surgery.

A medical procedure employing this hysteroscope 12 can be explained with reference to FIG. 5. The insertion tube 20 is vaginally inserted through the cervix 64 into the uterus 66 of a patient. The stream of saline solution 60 flows continuously to inflate the uterus 66 and, at the same time, to wash away any tissue particles destroyed by the laser beam 62. By manipulating the steering knobs 16, the surgeon can orient the steering section 26 and head 24 to steer the insertion tube into either horn 68 of the uterus. The insertion tube 20 and the steering knobs 16 are manipulated until any diseased or damaged tissue to be removed appears on the screen of the monitor 30. The laser fiber 34 is brought into contact with said tissue. The laser 32 is actuated and the laser beam 62 destroys the diseased tissue and cauterizes the wound. Any tissue debris resulting from this is washed away by the saline solution and flows out through the channel 50 when the valve 51 is depressed.

It should be apparent that with the hysteroscopic device of this invention, the insertion tube 20 can probe or penetrate deep into the uterus so that abnormal tissue can be removed or destroyed by laser microsurgery. This technique can eliminate the need for more drastic hysterectomies in many cases. Further, the video display on the monitor 30 permits observation by a team of surgeons. The surgeon can keep his or her face away from the affected area, thus avoiding the problem of contaminated fluids from the patient reaching the surgeon's eyes or skin.

This type of surgery, using an endoscopic guided laser fiber to perform microsurgery deep within the horns of the uterus is not possible with a standard rigid hysteroscope. The hysteroscope of this invention has only the two fluid tubes, i.e., the channel 56 for the high pressure saline stream to inflate the uterus 66 and the channel 50 which both drains the fluids and holds the laser optical fiber cable 34. The saline stream 60 is fed continuously and flows distally, not across the lens as with a typical gastroscope, for example. The articulation section 26 is kept as short as possible, and is limited to a maximum deflection angle of about thirty degrees to match the geometry of the uterus. Further, the insertion tube is kept short, about 25 cm, and has a predetermined uniform soft stiffness of about 0.2 pounds per inch for a four inch cantilevered length.

While the invention has been described in detail with reference to a single preferred embodiment, it should be understood that the invention is not limited to that embodiment. Rather, many modifications and variations would present themselves to those of skill in the art without departing from the scope and spirit of this invention, as defined in the appended claims.

What is claimed is:

1. A flexible video hysteroscope for the observation and treatment of abnormalities in the uterus of a female patient, comprising an insertion tube which includes a flexible elongated tubular member having a flexible outer sheath; a viewing head at the distal end of the tubular member and including imaging means in said head for viewing from said head; a biopsy channel extending within said tubular member to the distal and thereof and through said head, in which channel an elongated flexible laser fiber cable can be inserted to pass up to and out from said head, said laser fiber cable and biopsy channel defining a substantially annular fluid drainage channel that extends from the head to the proximal end of said elongated tubular member; a saline injection channel extending within said flexible tubular member to the distal end thereof and having means to receive a continuous flow of aqueous saline solution and an outlet port in said head directing the flow of saline solution distally therefrom; and an articulation section joining the head and the flexible tubular member and permitting controlled bending of the head with respect to the flexible tubular member, the bending being limited to a maximum angular deflection that corresponds to an angle at which horns of the uterus attach to the body thereof.

2. The video hysteroscope of claim 1 wherein said biopsy channel and said saline injection channel are the only fluid channels provided in said insertion tube.

3. The video hysteroscope of claim 1 in which said port provides a saline solution flow of substantially 100 cc/minute at a maximum pressure across the hysteroscope no greater than 155 mm Hg.

4. The video hysteroscope of claim 1 in which said viewing head has a distal front wall, and in a normal in-use orientation, said imaging means has a viewing port situated in said distal front wall above an exit port for said biopsy channel, and said saline injection channel port is situated in said distal wall vertically between the positions of the viewing port and exit port, and to one side thereof.

5. The video hysteroscope of claim 1 in which said insertion tube has a working length of substantially 25 cm.

6. The video hysteroscope of claim 1 in which said flexible tubular member has a uniform predetermined flexibility on the order of 0.05 to 1.0 lb/inch deflection for a 4 inch cantilevered length.

7. The video hysteroscope of claim 6 wherein said flexibility is substantially 0.2 lb/inch for a 4 inch cantilevered length.

8. The video hysteroscope of claim 1 further comprising a control section at the proximal end of said flexible tubular member and including means coupling said imaging means to a video monitor; steering means for selectively controlling the bending of said articulation section, and coupling means for connecting said saline channel to a source of said aqueous saline solution.

9. The video hysteroscope of claim 8 wherein said coupling means for said saline channel includes a Luer lock.

10. The video hysteroscope of claim 1 wherein said maximum angular deflection is substantially 30 degrees.

11. The video hysteroscope of claim 1 wherein said biopsy channel includes an outlet port at the proximal end of said tubular member and manually actuable valve permitting a practitioner to release fluids from the uterus through the biopsy channel end out the outlet port.

12. A method of treating a uterine abnormality comprising inserting through the cervix of a uterus of a female patient a flexible video hysteroscope that includes a flexible elongated tubular member having a flexible outer sheath, a viewing head at the distal end of the tubular member and including imaging means in said head for viewing from said head, a biopsy channel within said tubular member and extending within said tubular member to the distal end thereof and through said head, in which channel an elongated flexible laser fiber cable is inserted to extend up to and out from said head at an exit port therein, the laser fiber cable and biopsy channel defining a substantially annular fluid drainage channel that extends from said exit port to the proximal end of said elongated tubular member, a saline injection channel extending within said flexible tubular member to the distal end thereof and having means to receive a continuous flow of an aqueous saline solution and an outlet port in said head directing a flow of said saline solution distally therefrom, and an articulation section joining the head and the flexible tubular member and permitting controlled bending of the head with respect to the flexible tubular member; the bending being limited to a maximum angle on the order of about 30 degrees;

injecting said saline solution continuously through said saline injection channel into the uterus to inflate the same;

steering said head by selectively bending said articulation section until said abnormality is at a predetermined position in the viewing field of said imager; and irradiating said abnormality with laser radiation by means of the laser fiber cable in said biopsy channel.

13. The method of treating a uterine abnormality according to claim 12, further comprising draining fluids from said uterus through said annular fluid drainage channel defined by said laser fiber cable and said biopsy channel.

14. The method of treating a uterine abnormality according to claim 13, the step of draining fluids further including selectively actuating a valve on said biopsy channel to permit drainage out through an outlet port thereon.

* * * * *

UNITED STATES PATENT AND TRADEMARK OFFICE

CERTIFICATE OF CORRECTION

PATENT NO. : 4,836,189

DATED : June 6, 1989

INVENTOR(S) : ALLRED, III et al.

It is certified that error appears in the above-identified patent and that said Letters Patent is hereby corrected as shown below:

On the cover page, after Appl. No.:, please change "244,827" to --224,827--.

Col. 5, line 51, please change "and" to --end--.

Signed and Sealed this

Twentieth Day of March, 1990

Attest:

JEFFREY M. SAMUELS

*Attesting Officer*

*Acting Commissioner of Patents and Trademarks*